(12) United States Patent
Buchanan

(10) Patent No.: US 8,547,387 B2
(45) Date of Patent: Oct. 1, 2013

(54) SYSTEMS, METHODS AND APPARATUS TO UNAMBIGUOUSLY OUTLINE A REGION OF INTEREST

(75) Inventor: Robert Alan Buchanan, Dousman, WI (US)

(73) Assignee: General Electric Company, Schenectady, NY (US)

(*) Notice: Subject to any disclaimer, the term of this patent is extended or adjusted under 35 U.S.C. 154(b) by 1141 days.

(21) Appl. No.: 12/112,953

(22) Filed: Apr. 30, 2008

(65) Prior Publication Data

US 2009/0273608 A1 Nov. 5, 2009

(51) Int. Cl.
*G09G 5/02* (2006.01)
(52) U.S. Cl.
USPC .......................................... 345/589; 345/592
(58) Field of Classification Search
USPC ................................................. 345/589, 592
See application file for complete search history.

(56) References Cited

U.S. PATENT DOCUMENTS

| 6,747,665 | B1 | 6/2004 | Stovall | |
|---|---|---|---|---|
| 6,859,548 | B2* | 2/2005 | Yoshioka et al. | 382/128 |
| 2005/0256399 | A1* | 11/2005 | Sirohey et al. | 600/425 |
| 2008/0167551 | A1* | 7/2008 | Burns et al. | 600/427 |

* cited by examiner

*Primary Examiner* — Maurice L McDowell, Jr.
(74) *Attorney, Agent, or Firm* — The Small Patent Law Group; Dean D. Small

(57) ABSTRACT

Systems, methods and apparatus are provided through which in some implementations a graphical object is generated around a mathematical boundary of a region of interest in an image. The graphical object has varying opacity in which a higher opacity in areas of the graphical object in close proximity to the boundary acts as a visual cue to indicate close proximity to the boundary, and lesser opacity in areas of the graphical object of more distant proximity to the boundary acts as a visual cue to indicate distant proximity to the boundary.

22 Claims, 9 Drawing Sheets

US 8,547,387 B2

SYSTEMS, METHODS AND APPARATUS TO UNAMBIGUOUSLY OUTLINE A REGION OF INTEREST

FIELD OF THE INVENTION

This invention relates generally to healthcare imaging, and more particularly to visual depiction of regions of interest in healthcare images.

BACKGROUND OF THE INVENTION

Medical image viewing tools typically include features for delineating "regions of interest" (ROIs). An ROI is normally graphically indicated with a line outlining the shape of the region; sometimes a geometric shape such as an ellipse or rectangle, sometimes a hand drawn or algorithmically defined irregular shape. The line is known as a boundary. A boundary has no thickness or width, yet to visually depict or represent a boundary or a line, the boundary or line is visually depicted having a thickness or a width. By necessity, the thickness or width of the line overlays some part of the image. While various standards exist for the relationship between image data pixels and mathematical ROI boundaries, there is no agreed upon standard of how finite with graphical outlines map to the mathematical boundaries. Drawing the center line of the graphical object at the mathematical boundary is a common implementation, but other implementations place the mathematical boundary at the inside edge of the graphical outline.

When there is a need to indicate very precisely where the interior/exterior boundary, lies the thickness of the line used to mark the outline gives rise to ambiguity. A question arises as to whether the region boundary is located at the inside, middle, or outside of the line. Thus, visually depicting a boundary of a ROI using a line having a thickness or a width is inadequate.

BRIEF DESCRIPTION OF THE INVENTION

The above-mentioned shortcomings, disadvantages and problems are addressed herein, which will be understood by reading and studying the following specification.

The systems, methods and apparatus described herein provide increased precision for visual delineation of small or detailed objects in image display software. The systems, methods and apparatus described herein increases accuracy and speed of user perception due to lack of visual ambiguity.

Systems, methods and apparatus are provided through which in some implementations a graphical object is generated around a mathematical boundary of a region of interest of an image of an organ. The graphical object has varying opacity in which a higher opacity in areas of the graphical object in close proximity to the boundary acts as a visual cue to indicate close proximity to the boundary, and lesser opacity in areas of the graphical object of more distant proximity to the boundary acts as a visual cue to indicate distant proximity to the boundary.

In one aspect, a method to provide an unambiguous outline of a region of interest includes identifying a mathematical boundary of a region of interest of an organ in a healthcare image in a memory and the method includes generating a graphical object around the boundary in the image in the memory, the graphical object having varying degrees of opacity.

In another aspect, a computer-accessible medium has executable instructions capable of directing a processor to perform identifying a mathematical boundary of a region of interest of an organ in a healthcare image and generating a graphical object around the boundary in the image, the graphical object having varying degrees of opacity.

In yet another aspect, a system includes a processor, a storage device operable to store an image and the storage device being coupled to the processor and software apparatus operative on the processor to generate a graphical object around a boundary in the image, the graphical object having varying degrees of opacity.

Systems, clients, servers, methods, and computer-readable media of varying scope are described herein. In addition to the aspects and advantages described in this summary, further aspects and advantages will become apparent by reference to the drawings and by reading the detailed description that follows.

DETAILED DESCRIPTION OF THE INVENTION

In the following detailed description, reference is made to the accompanying drawings that form a part hereof, and in which is shown by way of illustration specific implementations which may be practiced. These implementations are described in sufficient detail to enable those skilled in the art to practice the implementations, and it is to be understood that other implementations may be utilized and that logical, mechanical, electrical and other changes may be made without departing from the scope of the implementations. The following detailed description is, therefore, not to be taken in a limiting sense.

The detailed description is divided into five sections. In the first section, a system level overview is described. In the second section, implementations of methods are described. In the third section, example output images are described. In the fourth section, hardware and operating environments in conjunction with which implementations may be practiced are described. Finally, in the fifth section, a conclusion of the detailed description is provided.

System Level Overview

Figure 1:
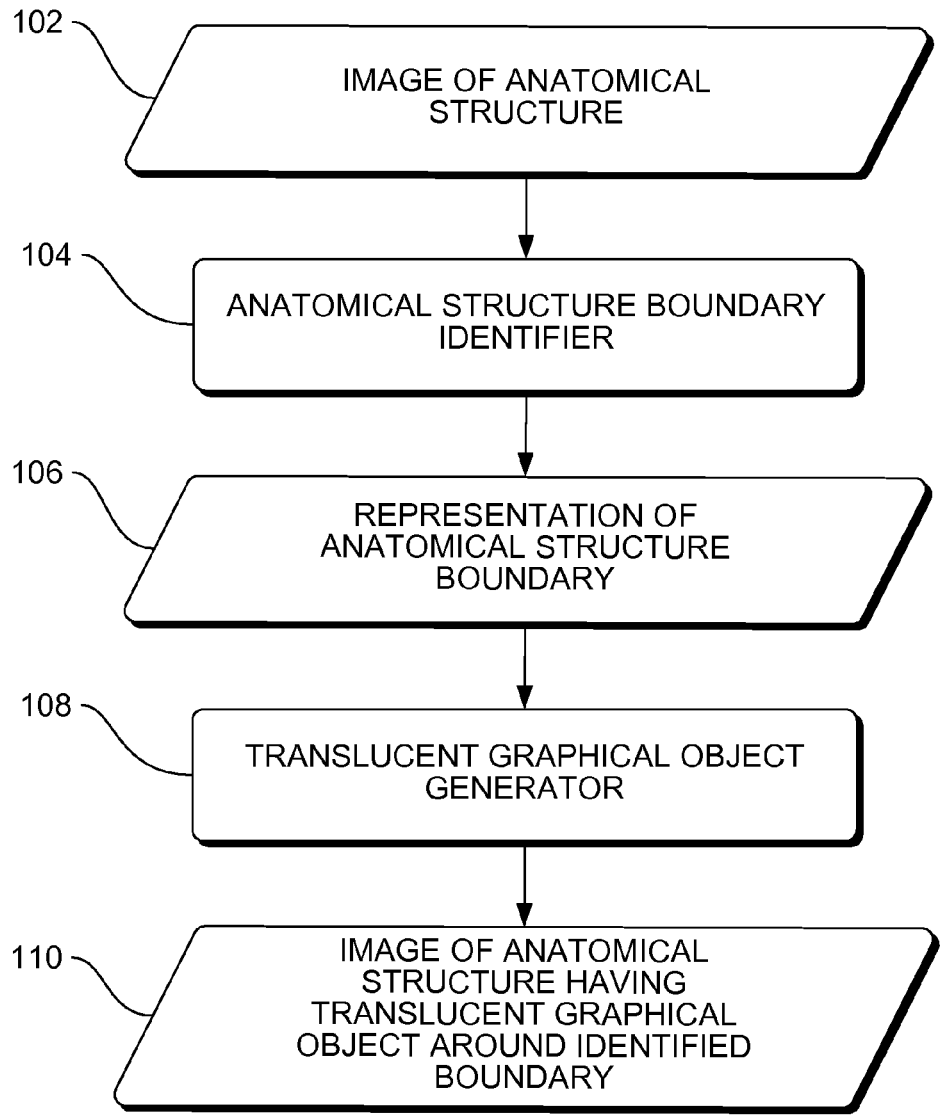
FIG. 1 is a block diagram of an overview of a system that provides an unambiguous outline of a boundary of an anatomical structure.

FIG. 1 is a block diagram of an overview of a system 100 that provides an unambiguous outline of a boundary of an anatomical structure. System 100 illustrates ROI boundaries by a graphical object of varying opacity with one (typically the inside) edge lying exactly along the mathematical region boundary. System 100 provides increased precision for visual delineation of small or detailed objects in image display software. System 100 increases accuracy and speed of user perception due to lack of visual ambiguity.

System 100 includes an image 102 of an anatomical structure. The image 102 can be acquired using any conventional healthcare imaging techniques, such as computed tomography (CT) (described in greater detail in FIG. 9), positron emission tomography (PET), hybrid CT/PET, magnetic resonance imaging (MRI) and ultrasound. Examples of an anatomical structure include organs such as a heart, lung, bronchial tube and brain. Other examples of an anatomical structure include arteries, bones and cartilage.

The image 102 of an anatomical structure is received by an anatomical structure boundary identifier 104. The anatomical structure boundary identifier 104 identifies, generates, recognizes and/or defines a representation 106 of a mathematical boundary of a region of interest in the image 102.

Figure 6:
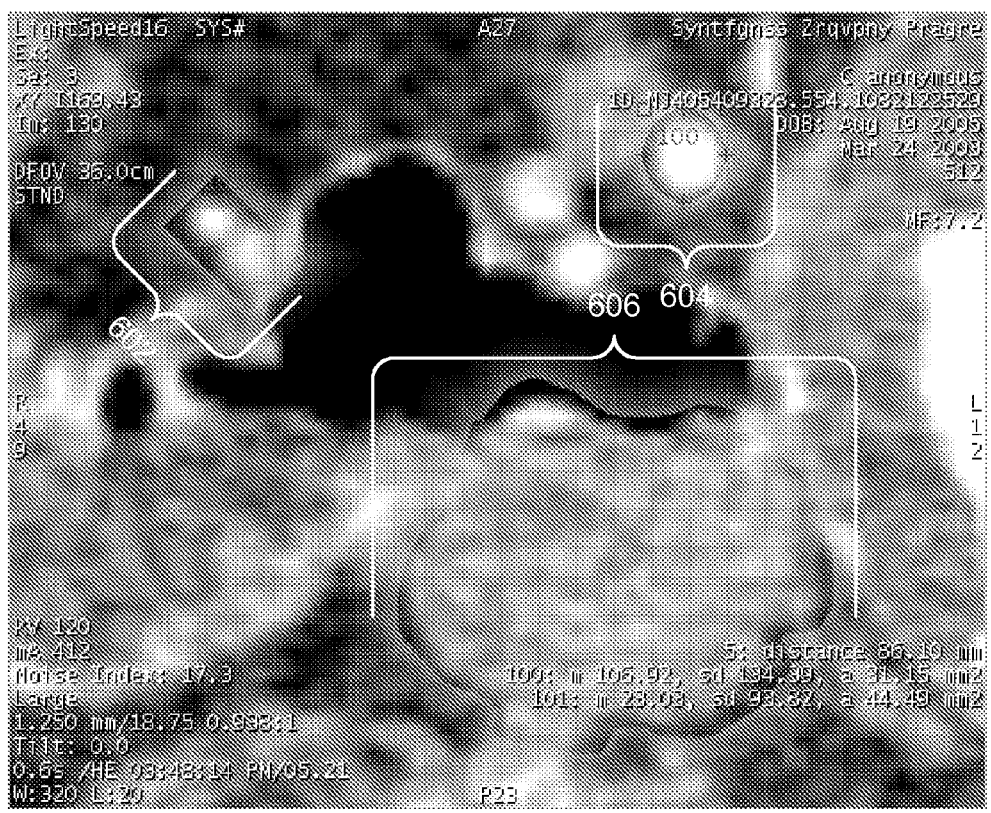
FIG. 6 is an example graphic representation having graphical notation of boundary of anatomical structures.
Figure 7:
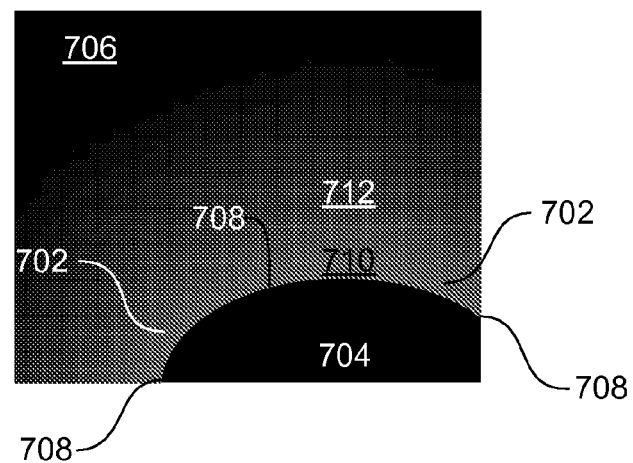
FIG. 7 is an example graphic representation having graphical notation of a portion of a boundary of an anatomical structure.

A translucent graphical object generator 108 generates a translucent border in the vicinity of the mathematical boundary of the region of interest of the organ in the image 102 from the representation 106 of the mathematical boundary. A result of the operation of the translucent graphical object generator 108 is an image 110 of the anatomical structure having a translucent graphic object in the vicinity of the identified boundary. The translucent graphic object has a color or pattern that is distinct from coloring of the region of interest, and the translucent graphic object has a color that is also distinct from a coloring of the background vicinity in the image so that the translucent graphic object is visually distinct from all surrounding areas in the close vicinity of the translucent graphic object. The translucent graphic object in the vicinity of the identified boundary in image 110 provides a visual cue to a reader of the image 110 that indicates unambiguously the position, shape and geometry of the boundary of the anatomical structure. Thus, the boundary does not need to be represented in the image by a thick line that ambiguously and indistinctly represents the boundary. Examples of an image 110 of an anatomical structure having a translucent graphical object around the boundary are shown in FIG. 6 and FIG. 7.

In some implementations, maximal opacity is used for the portion of the graphical object nearest the ROI boundary, with continuously and gradually decreasing opacity over several screen pixels more distant, eventually reducing to complete transparency or near complete transparency. The decreasing opacity gives the effect of a visual shape with one clearly defined edge corresponding exactly to the shape being illustrated, with the other edge "fading" to invisibility. Since the graphical object has only one visually distinguishable "edge" only one reasonable mapping between graphical object and ROI boundary exists, eliminating visual ambiguity.

The system 100 is not limited to any particular image 102 of an anatomical structure, anatomical structure boundary identifier 104, representation 106 of a mathematical boundary of a region of interest, translucent graphical object generator 108, and image 110 of the anatomical structure having a translucent graphic object in the vicinity of the identified boundary. For sake of clarity, system 100 describes a simplified image 102 of an anatomical structure, anatomical structure boundary identifier 104, representation 106 of a mathematical boundary of a region of interest, translucent graphical object generator 108, and image 110 of the anatomical structure having a translucent graphic object in the vicinity of the identified boundary.

The system level overview of the operation of an implementation is described above in this section of the detailed description. Some implementations operate in a multi-processing, multi-threaded operating environment on a computer, such as computer 830 in FIG. 8 and/or such as general computer environment 900 in FIG. 9.

Method Implementations

In the previous section, a system level overview of the operation of an implementation is described. In this section, the particular methods of such an implementation are described by reference to a series of flowcharts. Describing the methods by reference to a flowchart enables one skilled in the art to develop such programs, firmware, or hardware, including such instructions to carry out the methods on suitable computers, executing the instructions from computer-readable media. Similarly, the methods performed by the server computer programs, firmware, or hardware are also composed of computer-executable instructions. Methods 200-500 are performed by a program executing on, or performed by firmware or hardware that is a part of, a computer, such as computer 830 in FIG. 8 and/or such as general computer environment 900 in FIG. 9.

Figure 2:
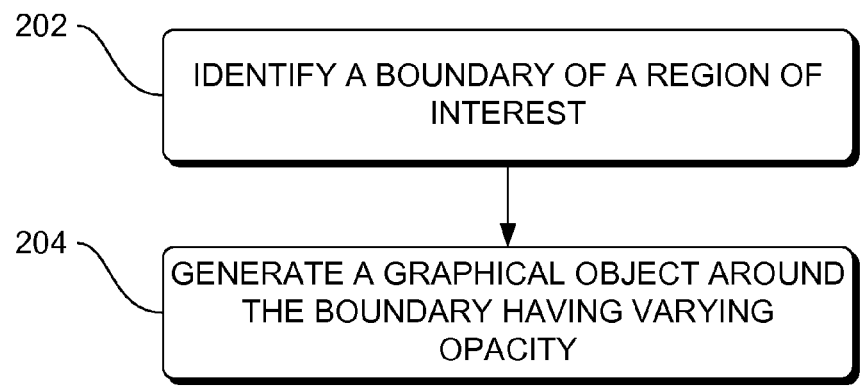
FIG. 2 a flowchart of a method that provides an unambiguous outline around a boundary of a region of interest in a health-care image, according to an implementation.

FIG. 2 a flowchart of a method 200 that provides an unambiguous outline around a boundary of a region of interest (ROI) in a health-care image, according to an implementation. Method 200 describes a graphical technique for outlining an ROI in such a way as to eliminate ambiguity in the location, shape and geometry of a boundary between the region of interest and the remainder of the image. In general, the outlining surrounds the ROI with an outline of decreasing opacity as the outline becomes more distant from the mathematically defined boundary. The decreasing opacity provides the visual effect of a border with a clearly defined inner edge (corresponding to the mathematical boundary) but having no discernable outside edge.

Some implementations of method 200 include identifying, generating, recognizing and/or defining a mathematical boundary of a region of interest (ROI) of an organ in a health-care image, and block 202. In some implementations, the mathematical boundary of the ROI is identified, generated, recognized and/or defined using existing techniques, e.g. geometric shapes or spline curves, in such a way that inside/outside and distance from boundary can be computed for any given point. In some implementations, the image is stored in a memory such as random-access memory 912 in FIG. 9.

Method 200 also includes generating a graphical object near the boundary in the image in the memory, at block 204. The graphical object has varying degrees and/or extent of opacity. Variations of opacity are described in FIG. 3. In some implementations the graphical object having opacity is generated outside the boundary. In some implementations, the graphic object having opacity is generated inside the boundary. An implementation of generating a graphical object near the boundary in the image is described in FIG. 5.

Figure 3:
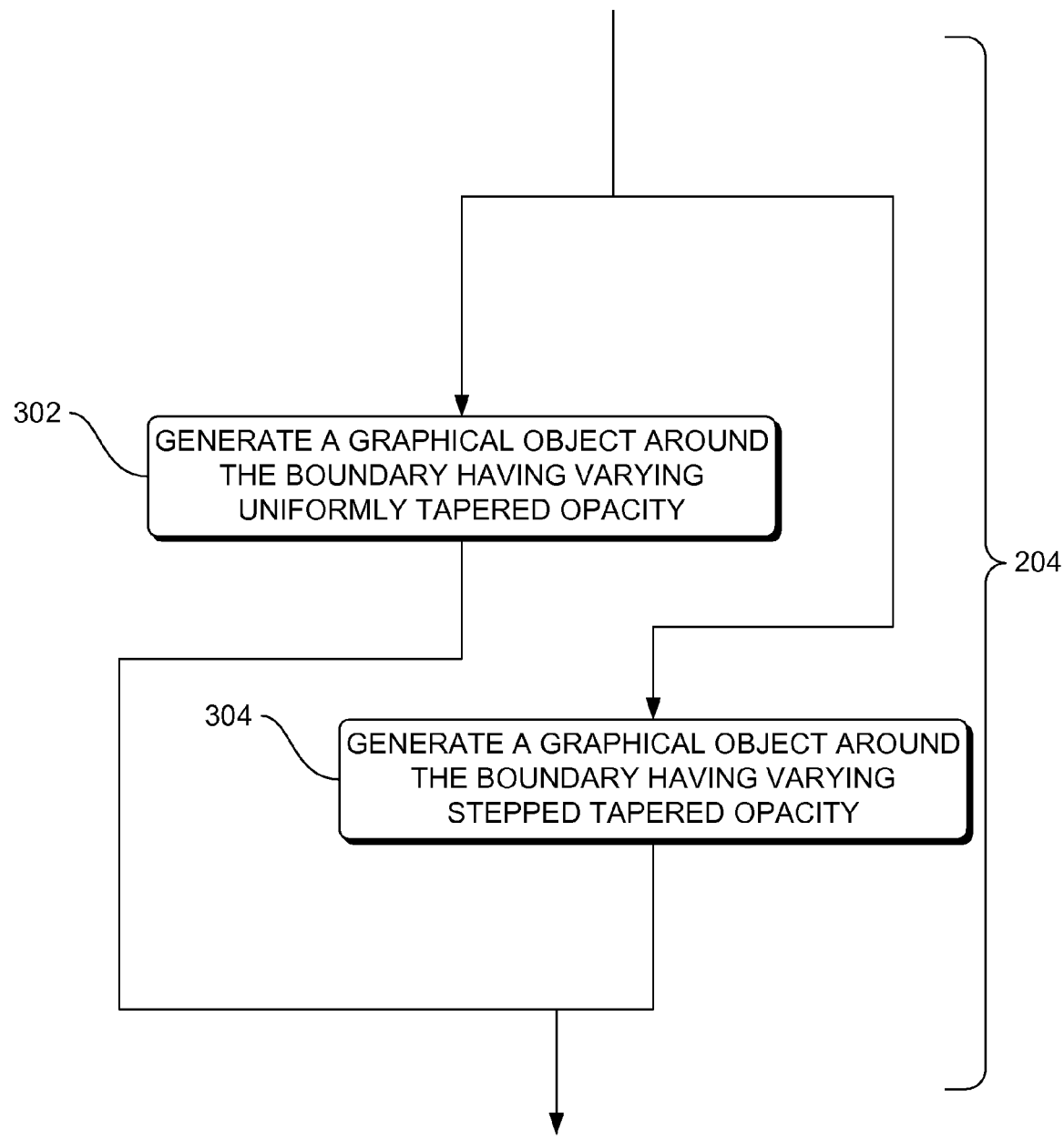
FIG. 3 is a flowchart of a method of generating a graphic object around the boundary having variations in opacity, according to various implementations.

FIG. 3 is a flowchart of a method 300 of generating a graphic object around the boundary having variations in opacity, according to various implementations. Method 300 provides implementations of generating a graphic object at block 204 in FIG. 2.

Method 300 includes generating a graphical object around the boundary having opacity that varies and tapers uniformly, at block 302. The graphical object around the boundary starts in maximum opacity (e.g. opaque or near opaque) at locations nearest the boundary and tapers uniformly to complete transparency or near complete transparency in a direction away from the boundary. The variation in opacity from maximum opacity to complete transparency varies uniformly. FIG. 6 and FIG. 7 show examples of a graphical object that tapers uniformly from the boundary and outward therefrom.

Method 300 includes generating a graphical object around the boundary having opacity that varies and tapers in steps, at block 304. The graphical object around the boundary starts in maximum opacity (e.g. opaque or near opaque) at locations nearest the boundary and tapers in steps to complete transparency in a direction away from the boundary. The variation in opacity from maximum opacity to complete transparency varies in steps. In some implementations, the thickness of the different degrees of opacity in each of the steps is not visually noticeable to a human. For example, in one implementation, the thickness of each step is approximately one pixel. In some implementations, the thickness of the different degrees of opacity in each of the steps is visually noticeable to a human. For example, in one implementation, the thickness of each step is approximately ½oth of an inch.

Figure 4:
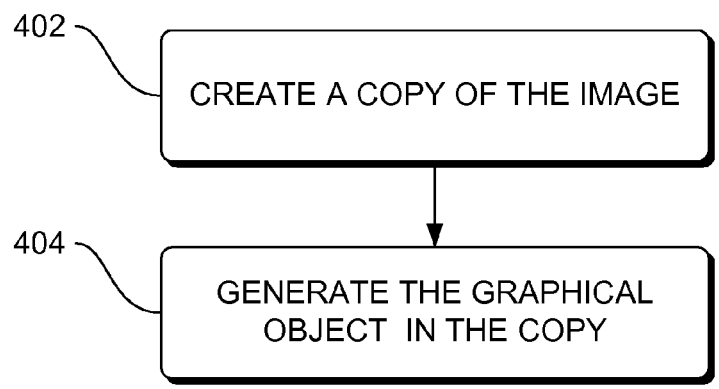
FIG. 4 is a flowchart of a method generates a boundary outlining graphical object to copy of an original image, according to an implementation.

FIG. 4 is a flowchart of a method 400 generates a boundary outlining graphical object to copy of an original image, according to an implementation. Method 400 provides actions that allow a new image to be generated with the graphical object having varying opacity.

Method 400 includes creating a copy of the image 102 of the anatomical structure, at block 402. Method 400 also includes generating the graphical object in the copy, at block 404. Action 404 replaces action 204 in FIG. 2. In some implementations action 402 is performed before method 200 begins. In other implementations action 402 is performed any time before action 404, such as after action 202.

Figure 5:
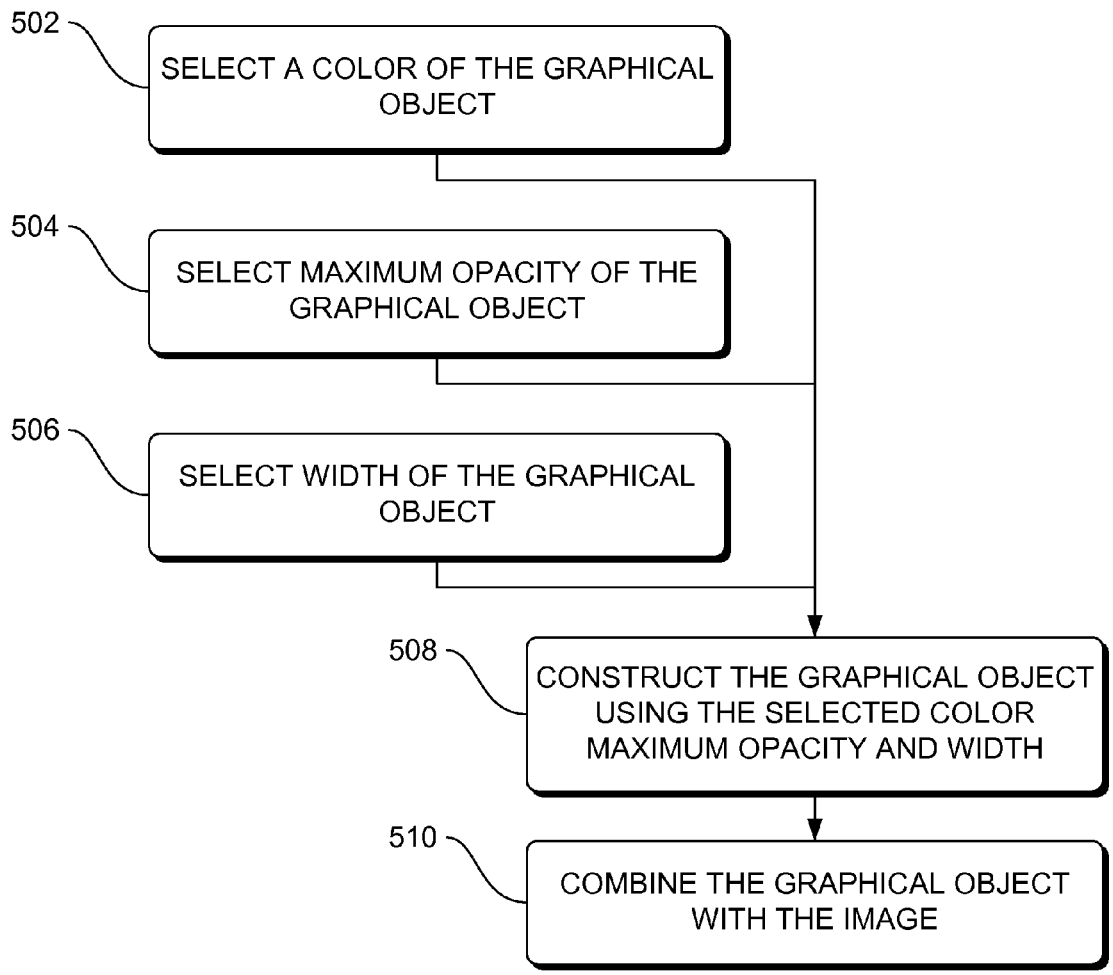
FIG. 5 is a flowchart of a method of generating a graphic object around the boundary having variations in opacity, according to various implementations.

FIG. 5 is a flowchart of a method 500 of generating a graphic object around the boundary having variations in opacity, according to various implementations. Method 500 is an implementation of generating a graphic object at block 204 in FIG. 2.

Some implementations of method 500 include selecting an RGB (red/green/blue intensity) color value for region highlighting of the graphical object, at block 502. In some implementations, the color value is a color that is unlikely to occur at any point in the image 102 of the anatomical structure near the ROI. For an image 102 composed of grayscale medical images, a fully saturated color (e.g. red, orange, yellow, green, etc) is a color that is unlikely to occur at any point in the image 102.

Some implementations of method 500 also include selecting a maximum opacity (e.g. opaque or near opaque) for the portions of the region highlight of the graphical object nearest the ROI boundary, at block 504. The maximum opacity can be referred to as an alpha channel value. The maximum opacity can be selected so as to make the highlighting color visually readily apparent when placed over the base image, yet not obscure detail within the image 102.

Translucence is typically described in terms of opacity or alpha channel value (alpha), that are more or less interchangeable terms to describe the inverse of transparency. Opacity is often expressed either as a percentage: 100%=fully opaque, 0% completely transparent or a value from 1.0 (i.e. completely opaque) to 0.0 (i.e. completely transparent). Alpha is another term for the exact same concept, though the term "alpha" is more likely to be used in a context where a numerical representation scheme for image pixels is assumed. A common convention for the numerical representation scheme of image pixels using a 32-bit binary number for each pixel with the first eight bits, capable of representing a value from 0 to 255, encoding the alpha (opacity) and the next three groups of eight representing the intensities of the red, green and blue components respectively. For example 75% opaque red might be described as "0.75 translucent red", less commonly as "25% transparent red" or encoded in "32-bit ARGB" as 191/255/0/0, meaning alpha 191 of a possible 255, red 255 of 255, etc.

Some implementations of method 500 also include selecting a highlight width, at block 506. In some implementations the width of the graphical object is selected to be sufficient to produce a clear visual border around the ROI and wide enough to permit a smooth visual fading effect (to be generated below) yet narrow enough to avoid interactions with portions of the base image distant from the ROI. In some implementations the width of the graphical object is selected to be 5-20 pixels.

The actions of selecting the color, 502, selecting the opacity 504 and selecting the width 506 of the graphical object can be performed in any order.

Some implementations of method 500 include constructing an ROI highlighting overlay graphical object image with color equal to the selected color and opacity, at block 508. In some embodiments the graphical object is generated or constructed separately from the image 102 and using a matching coordinate system. In some embodiments the graphical object is constructed with an opacity of zero inside the ROI, an opacity of zero for points outside the ROI and more than the highlight width distant from the ROI boundary and in opacity for points outside and near the region assign opacity so the opacity is at the chosen maximum for distance zero, zero at a distance equal to the highlight width, and inversely proportional to distance from the ROI boundary in between.

In one implementation of the constructing at block 508, for every pixel in the bounds of the image, assign an RGB value directly and compute an alpha value of the RGB value. Note that standard techniques for smoothing the inner edge of the ROI highlight, e.g. decreasing alpha values proportionally to account for pixels partially inside and partially outside the ROI, can also be applied as desired.

In one implementation of the constructing at block 508, conventional mathematical techniques are implemented for generating dilated (i.e. expanded in conventional computer graphics terminology) regions of the same shape as the ROI in a succession of sizes up to the region width larger than the ROI. For each dilated region, starting with the largest, filling the overlay image pixels within that region to the chosen RGB value and an alpha inversely proportional to its dilation width, using a Porter-Duff "Source" rule (again, in conventional computer graphics terminology). Finally, clearing the ROI to zero opacity, optionally smoothing for partial pixels in a conventional manner.

Thereafter, method 500 includes combining the generated overlay graphical object with the image 102 to form a final composite image, at block 510. In some implementations the combining 510 is performed using the Porter-Duff "Source Over" rule, with the base image as destination and the overlay image as source.

In an alternative implementation, the equivalent image is generated directly on the image 102, without creating a separate overlay image.

Figure 9:
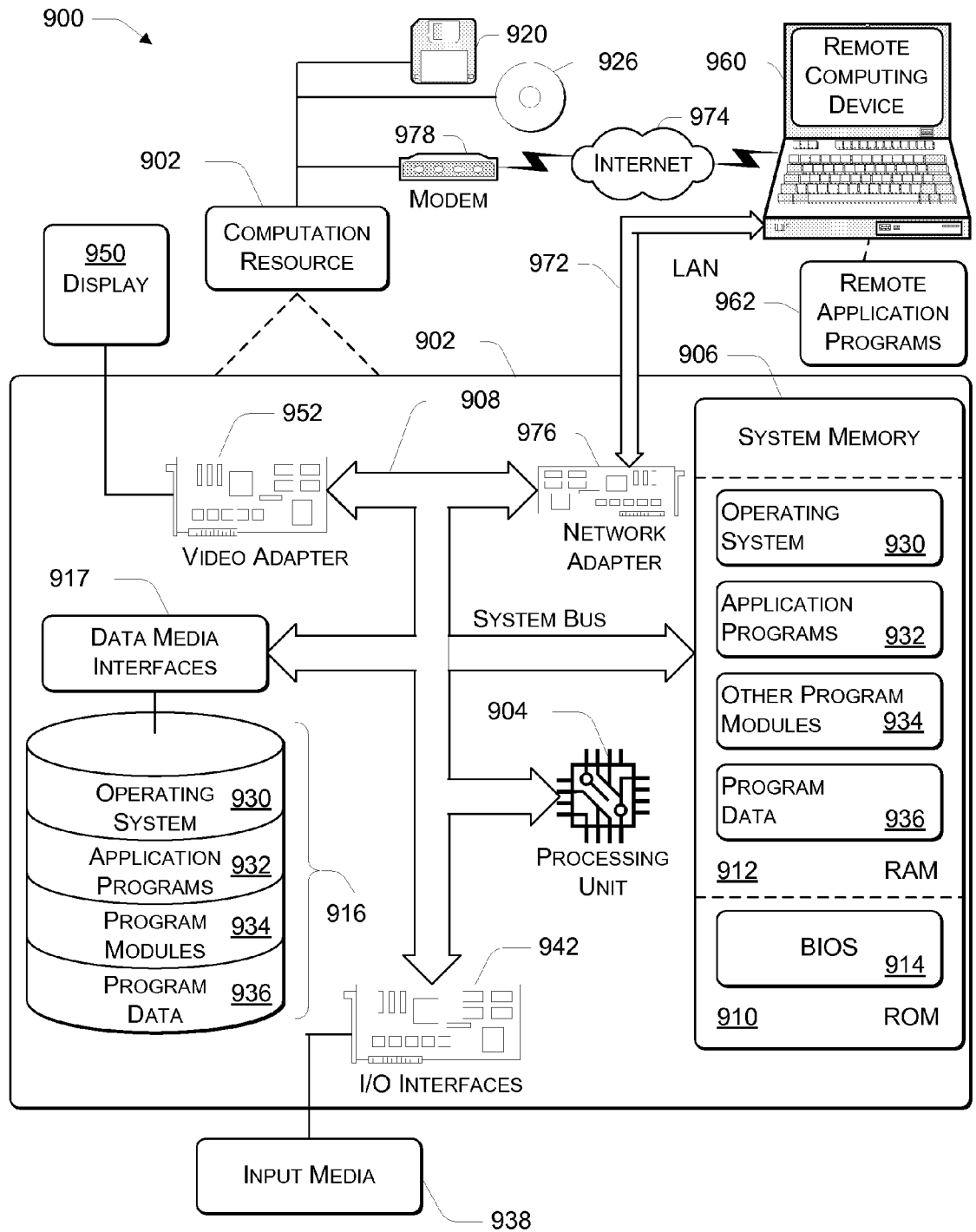
FIG. 9 is a block diagram of a general computer environment in which different implementations can be practiced.

In some implementations, methods 200-500 are implemented as a computer data signal embodied in a carrier wave, that represents a sequence of instructions which, when executed by a processor, such as processing unit 904 in FIG. 9, cause the processor to perform the respective method. In other implementations, methods 200-500 are implemented as a computer-accessible medium having executable instructions capable of directing a processor, such as processing units 904 in FIG. 9, to perform the respective method. In varying implementations, the medium is a magnetic medium, an electronic medium, or an optical medium.

Example Output Images

This section of the detailed description describes example output images if FIG. 6 and FIG. 7.

FIG. 6 is an example graphic representation 600 having a graphical notation of boundary of anatomical structures. FIG. 6 illustrates examples of the output of system 100 and methods 200-500. FIG. 6 includes three anatomical structures, 602, 604 and 606 that have graphical objects outside of the boundaries of the anatomical structures that have varying opacity to indicate the position, shape and geometry of the boundary of each anatomical structure. Each of the graphical objects in FIG. 6 illustrates the result of action 302 in FIG. 3, in which each graphical object has opacity of uniform tapering. The graphical object fades uniformly from maximum or near maximum opacity (e.g. opaque or near opaque) in the immediate vicinity of the boundary to complete transparency or near transparency further away from the boundary. The extent or degree of opacity in the graphical object decreases at distances further away from the boundary. Each of the graphical objects in FIG. 6 have a color that is distinct from coloring of the region of anatomical structure, and the translucent graphic object has a color that is also distinct from a coloring of the background vicinity in the image so that the translucent graphic object is visually distinct from all surrounding areas in the close vicinity of the translucent graphic object.

FIG. 7 is an example graphic representation 700 having a graphical notation of a portion of a boundary of an anatomical structure. FIG. 7 illustrates an example of a portion of the output of system 100 and methods 200-500. FIG. 7 includes a portion of the anatomical structure 606 that has a graphical object outside of the boundary of the anatomical structure that has varying opacity to indicate the position, shape and geometry of the boundary of the anatomical structure.

In FIG. 7, the graphical object 702 is the highlighted area. The anatomical structure 704 is the dark inner area. The background 706 is the dark outer area outside of the graphical object 702. In the boundary 708 is the line between the graphical object 702 and the anatomical structure 704. The boundary 708 is a line having no breadth or thickness.

The graphical object 702 fades uniformly from complete or near maximum opacity (e.g. opaque or near opaque) in the immediate vicinity 710 of the boundary 708 to complete transparency or near complete transparency 712 further away from the boundary 708. The extent or degree of opacity in the graphical object decreases at distances further away from the boundary 708. The graphical object 702 in FIG. 7 has a color (e.g. teal as shown) that is distinct from coloring (e.g. black as shown) of the region of anatomical structure 704. The translucent graphic object 704 has a color (e.g. teal as shown) that is also distinct from a coloring (e.g. black as shown) of the background vicinity 706 in the image so that the translucent graphic object 702 is visually distinct from all surrounding areas in the close vicinity of the translucent graphic object 702.

The graphical object 702 in FIG. 7 illustrates the result of action 302 in FIG. 3, in which the graphical object 702 has opacity of uniform tapering.

Hardware and Operating Environment

Figure 8:
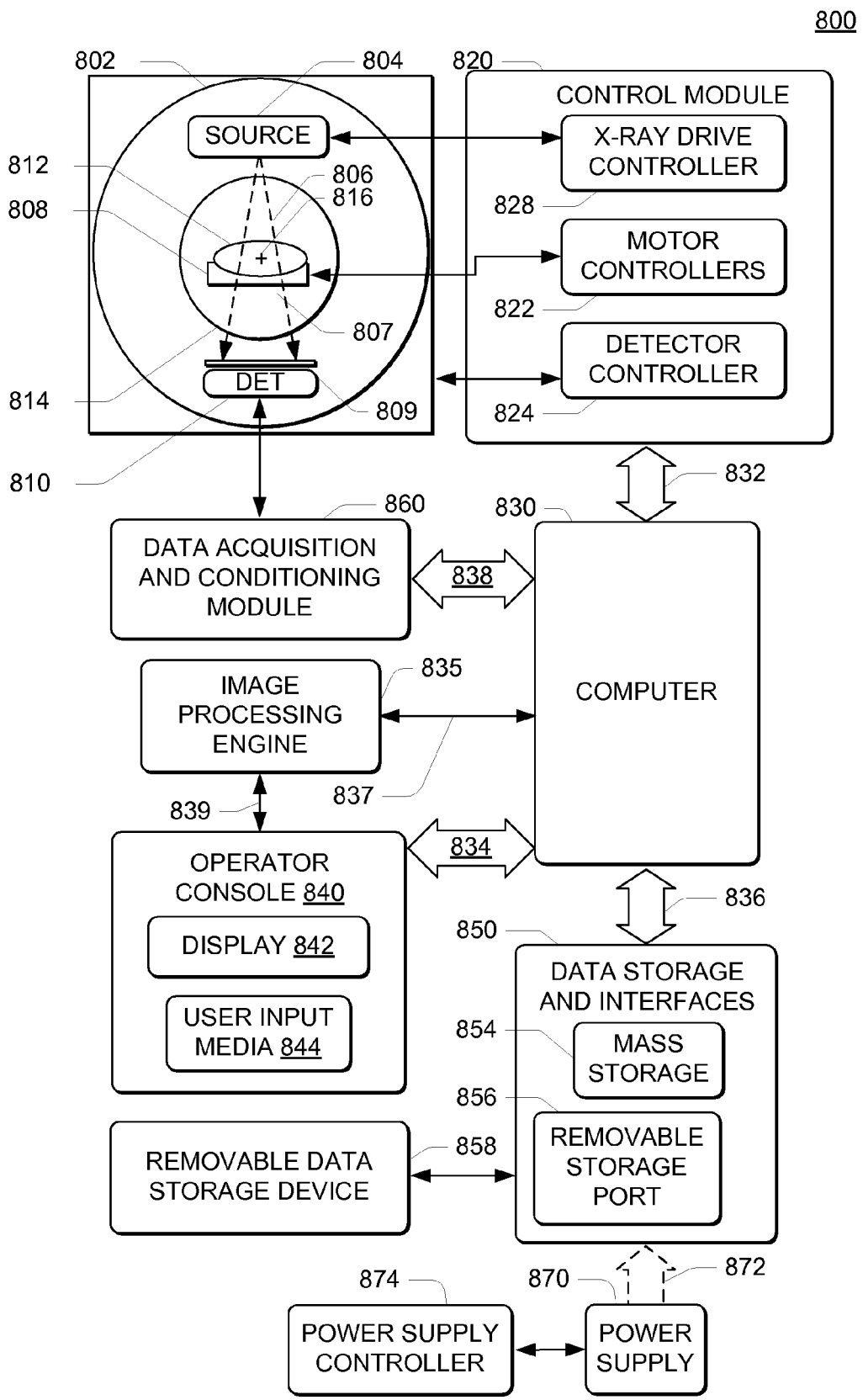
FIG. 8 is a simplified diagram of an overview of a modified system configured to improve X-ray imaging operations.

FIG. 8 is a simplified diagram of an overview of a modified system 800 configured to improve X-ray imaging operations. The system 800 optionally includes a gantry 802 or other support for an illumination source 804, such as an X-ray illumination source, capable of providing illumination 806, such as X-rays or other non-destructive internal imaging illumination, and can optionally include a test subject support 808 that is transmissive with respect to the illumination 806 and that is positioned above a scintillator 809 and detector 810 that is also opposed to the illumination source 804. Alternatively, a direct conversion detector 810 can be employed without need for a scintillator.

In one implementation, components of the system 800 and a test subject 812 are maintained in a defined geometric relationship to one another by the gantry 802. A distance between the illumination source 804 and the detector 810 can be varied, depending on the type of examination sought, and the angle of the illumination 806 respective to the test subject 812 can be adjusted with respect to the body to be imaged responsive to the nature of imaging desired.

In one implementation, the test subject support 808 is configured to support and/or cause controlled motion of the test subject 812, such as a living human or animal patient, or other test subject 812 suitable for non-destructive imaging, above the scintillator 809/detector 810 so that illumination 807 is incident thereon after passing through the test subject 812. In turn, information from the detector array 810 describes internal aspects of the test subject 812.

The scintillator 809 can be a conventional CsI scintillator 809, optically coupled to an array of photodiodes (not illustrated), such as a two-dimensional array of photodiodes and suitable control transistors formed using semiconductor material such as amorphous silicon, or any other form of detector 810 suitable for use with the type or types of illumination 806 being employed, such as X-rays. The detector elements are typically tesselated in a mosaic. The scintillator 809 converts incident photons comprising electromagnetic radiation, such as X-rays, from high-energy, high-frequency photons 807, into lower-energy, lower-frequency photons corresponding to spectral sensitivity of the detector elements, in a fashion somewhat analogous to fluorescence, as is commonly known in the context of many visible-light sources in use today. Alternatively, the detector 810 can be formed as a flat-panel array including amorphous Silicon (α-Si) active elements, together with either a scintillator layer 809, or a direct converter material such as Cadmium Zinc Telluride (CdZnTe), Mercuric Iodide ($HgI_2$), Lead Iodide ($PbI_2$), or amorphous Selenium (α-Se).

In some modes of operation, such as CT, the gantry 802 and test subject support or table 808 cooperatively engage to move the test subject 812 longitudinally within an opening 814, that is, along an axis 816 extending into and out of the plane of FIG. 8. In some modes of operation, the gantry 802 rotates the X-ray source 804 and detector 810 about the axis 816, while the support 808 moves longitudinally, to provide a helical series of scans of the test subject 812, where a pitch of the helices is defined as a ratio of a longitudinal distance traveled by the table 808 during a complete revolution of the gantry 802, compared to a length of the detector 810 along the axis 816 of linear motion.

The system 800 also optionally includes a control module or controller 820. The controller 820 can include a motor control module 822 configured to move the test subject support 808 and thus the test subject 812 relative to the X-ray source 804 and/or detector 810, and can also control motors in the gantry 802 or to position the X-ray illumination source 804 relative to the test subject 812 and/or the detector 810.

The controller 820 includes a detector controller 824 configured to control elements within the detector 810 and to facilitate data transfer therefrom. The controller 820 also includes a drive parameter controller 828 configured to control electrical drive parameters delivered to the X-ray source 804. One or more computers 830 provide connections to the controller 820 via a bus 832 configured for receiving data descriptive of operating conditions and configurations and for supplying appropriate control signals. Buses 834, 837 and 839 act to transfer data and control signals, for example with respect to a module 835, configured as an image processing engine, via interconnections such as 837, 839 that are configured for exchange of signals and data to and/or from the computer 830 as well as other elements of the system 800 and/or external computation or communications resources (not illustrated in FIG. 8).

The system 800 also includes a bus 836, a bus 838 and an operator console 840. The operator console 840 is coupled to the system 800 through the bus 834. The operator console 840 includes one or more displays 842 and a user input interface 844. The user input interface 844 can include a touchscreen, keyboard, a mouse or other tactile input device, capability for voice commands and/or other input devices. The one or more displays 842 provide video, symbolic and/or audio information relative to operation of system 800, user-selectable options and images descriptive of the test subject 812, and can display a graphical user interface for facilitating user selection among various modes of operation and other system settings.

The image processing engine 835 facilitates automation of accurate measurement and assessment. The image processing engine 835 is capable of forming multiple, coordinated images for display, for example via the monitor 842, to provide the types of depictions described below. The image processing engine 835 can comprise a separate and distinct module, which can include application-specific integrated circuitry, or can comprise one or more processors coupled with suitable computer-readable program modules, or can comprise a portion of the computer 830 or other computation device.

The system 800 also includes memory devices 850, coupled via the bus 836 to the computer 830 through suitable interfaces. Datasets representing three-dimensional data and image or two-dimensional data typically conform to the digital imaging and communications in medicine (DICOM) standard, which is widely adopted for handling, storing, printing, and transmitting information in medical imaging. The DICOM standard includes a file format definition and a network communications protocol. The communication protocol is an application protocol that uses TCP/IP to communicate between systems. DICOM files can be stored in memory devices 850 and retrieved therefrom, and can be exchanged between two entities that are capable of receiving image and patient data in DICOM format.

The memory devices 850 include mass data storage capabilities 854 and one or more removable data storage device ports 856. The one or more removable data storage device ports 856 are adapted to detachably couple to portable data memories 858, which can include optical, magnetic and/or semiconductor memories and can have read and/or write capabilities, and which can be volatile or non-volatile devices or can include a combination of the preceding capabilities.

The system 800 further includes a data acquisition and conditioning module 860 that has data inputs coupled to the detector 810 and that is coupled by the bus 838 to the one or more computers 830. The data acquisition and conditioning module 860 includes analog to digital conversion circuitry for capturing analog data from the detector 810 and then converting those data from the detector 810 into digital form, to be supplied to the one or more computers 830 for ultimate display via at least one of the displays 842 and for potential storage in the mass storage device 854 and/or data exchange with remote facilities (not shown in FIG. 8). The acquired image data can be conditioned in either the data acquisition and conditioning module 860 or the one or more computers 830 or both.

The system 800 also includes a power supply 870, coupled via interconnections represented as a power supply bus 872, shown in dashed outline, to other system elements, and a power supply controller 874. In some implementations, the system 800 is configured to be a mobile system equipped with a portable power supply 870, such as a battery. In other words, the system 800 can comprise a wheeled unit and can be electromotively powered in self-contained fashion, lending physical agility to the ensemble of attributes offered by the system 800.

Volumetric data collected via exposure of the test subject 812 to suitable illumination 806 can be processed via many different types of tools, each intended to enhance some portion of information content described by the data. One result can be inconsistency between analytical results from different types of signal processing tools, or between measurement results corresponding to different measurement times and/or measurement phases.

FIG. 9 is a block diagram of a general computer environment 900 in which different implementations can be practiced. The description of FIG. 9 provides an overview of computer hardware and a suitable computing environment in conjunction with which some implementations can be implemented. Implementations are described in terms of a computer executing computer-executable instructions. However, some implementations can be implemented entirely in computer hardware in which the computer-executable instructions are implemented in read-only memory. Some implementations can also be implemented in client/server computing environments where remote devices that perform tasks are linked through a communications network. Program modules can be located in both local and remote memory storage devices in a distributed computing environment.

FIG. 9 illustrates an example of a general computer environment 900 useful in the context of the environment of FIG. 8, in accordance with an implementation of the disclosed subject matter.

The illustrated operating environment 900 is only one example of a suitable operating environment, and the example described with reference to FIG. 9 is not intended to suggest any limitation as to the scope of use or functionality of the implementations of this disclosure. Other well-known computing systems, environments, and/or configurations can be suitable for implementation and/or application of the subject matter disclosed herein.

The general computer environment 900 includes a computation resource 902 capable of implementing the processes described herein. It will be appreciated that other devices can alternatively used that include more components, or fewer components, than those illustrated in FIG. 9.

The computation resource 902 includes one or more processors or processing units 904, a system memory 906, and a bus 908 that couples various system components including the system memory 906 to processor(s) 904 and other elements in the environment 900. The bus 908 represents one or more of any of several types of bus structures, including a memory bus or memory controller, a peripheral bus, an accelerated graphics port and a processor or local bus using any of a variety of bus architectures, and can be compatible with SCSI (small computer system interconnect), or other conventional bus architectures and protocols.

The system memory 906 includes nonvolatile read-only memory (ROM) 910 and random access memory (RAM) 912, which can or can not include volatile memory elements. A basic input/output system (BIOS) 914, containing the elementary routines that help to transfer information between elements within computation resource 902 and with external items, typically invoked into operating memory during start-up, is stored in ROM 910.

The computation resource 902 further can include a non-volatile read/write memory 916, represented in FIG. 9 as a hard disk drive, coupled to bus 908 via a data media interface 917 (e.g., a SCSI, ATA, or other type of interface); a magnetic disk drive (not shown) for reading from, and/or writing to, a removable magnetic disk 920 and an optical disk drive (not shown) for reading from, and/or writing to, a removable optical disk 926 such as a CD, DVD, or other optical media.

The non-volatile read/write memory 916 and associated computer-readable media provide nonvolatile storage of computer-readable instructions, data structures, program modules and other data for the computation resource 902. Although the exemplary environment 900 is described herein as employing a non-volatile read/write memory 916, a removable magnetic disk 920 and a removable optical disk 926, it will be appreciated by those skilled in the art that other types of computer-readable media which can store data that is accessible by a computer, such as magnetic cassettes, FLASH memory cards, random access memories (RAMs), read only memories (ROM), and the like, can also be used in the exemplary operating environment.

A number of program modules can be stored via the non-volatile read/write memory 916, magnetic disk 920, optical disk 926, ROM 910, or RAM 912, including an operating system 930, one or more application programs 932, other program modules 934 and program data 936. Examples of computer operating systems conventionally employed for some types of three-dimensional and/or two-dimensional medical image data include the NUCLEUS® operating system, the LINUX® operating system, and others, for example, providing capability for supporting application programs 932 using, for example, code modules written in the C++® computer programming language.

A user can enter commands and information into computation resource 902 through input devices such as input media 938 (e.g., keyboard/keypad, tactile input or pointing device, mouse, foot-operated switching apparatus, joystick, touch-screen or touchpad, microphone, antenna etc.). Such input devices 938 are coupled to the processing unit 904 through a conventional input/output interface 942 that is, in turn, coupled to the system bus. A monitor 950 or other type of display device is also coupled to the system bus 908 via an interface, such as a video adapter 952.

The computation resource 902 can include capability for operating in a networked environment (as illustrated in FIG. 8, for example) using logical connections to one or more remote computers, such as a remote computer 960. The remote computer 960 can be a personal computer, a server, a router, a network PC, a peer device or other common network node, and typically includes many or all of the elements described above relative to the computation resource 902. In a networked environment, program modules depicted relative to the computation resource 902, or portions thereof, can be stored in a remote memory storage device such as can be associated with the remote computer 960. By way of example, remote application programs 962 reside on a memory device of the remote computer 960. The logical connections represented in FIG. 9 can include interface capabilities, e.g., such as interface capabilities 852 (FIG. 8) a storage area network (SAN, not illustrated in FIG. 9), local area network (LAN) 972 and/or a wide area network (WAN) 974, but can also include other networks.

Such networking environments are commonplace in modern computer systems, and in association with intranets and the Internet. In certain implementations, the computation resource 902 executes an Internet Web browser program (which can optionally be integrated into the operating system 930), such as the "Internet Explorer®" Web browser manufactured and distributed by the Microsoft Corporation of Redmond, Wash.

When used in a LAN-coupled environment, the computation resource 902 communicates with or through the local area network 972 via a network interface or adapter 976. When used in a WAN-coupled environment, the computation resource 902 typically includes interfaces, such as a modem 978, or other apparatus, for establishing communications with or through the WAN 974, such as the Internet. The modem 978, which can be internal or external, is coupled to the system bus 908 via a serial port interface.

In a networked environment, program modules depicted relative to the computation resource 902, or portions thereof, can be stored in remote memory apparatus. It will be appreciated that the network connections shown are exemplary, and other means of establishing a communications link between various computer systems and elements can be used.

A user of a computer can operate in a networked environment 800 using logical connections to one or more remote computers, such as a remote computer 960, which can be a personal computer, a server, a router, a network PC, a peer device or other common network node. Typically, a remote computer 960 includes many or all of the elements described above relative to the computer 900 of FIG. 9.

The computation resource 902 typically includes at least some form of computer-readable media. Computer-readable media can be any available media that can be accessed by the computation resource 902. By way of example, and not limitation, computer-readable media can comprise computer storage media and communication media.

Computer storage media include volatile and nonvolatile, removable and non-removable media, implemented in any method or technology for storage of information, such as computer-readable instructions, data structures, program modules or other data. The term "computer storage media" includes, but is not limited to, RAM, ROM, EEPROM, FLASH memory or other memory technology, CD, DVD, or other optical storage, magnetic cassettes, magnetic tape, magnetic disk storage or other magnetic storage devices, or any other media which can be used to store computer-intelligible information and which can be accessed by the computation resource 902.

Communication media typically embodies computer-readable instructions, data structures, program modules or other data, represented via, and determinable from, a modulated data signal, such as a carrier wave or other transport mechanism, and includes any information delivery media. The term "modulated data signal" means a signal that has one or more of its characteristics set or changed in such a manner as to encode information in the signal in a fashion amenable to computer interpretation.

By way of example, and not limitation, communication media include wired media, such as wired network or direct-wired connections, and wireless media, such as acoustic, RF, infrared and other wireless media. The scope of the term computer-readable media includes combinations of any of the above.

The computer 902 can function as one or more of the control segments of module 820 (FIG. 8), the computer 830, the operator console 840 and/or the data acquisition and conditioning module 860, for example, via implementation of the apparatus in FIG. 1 and the processes in FIGS. 2-5, respectively, as one or more computer program modules.

Apparatus in FIG. 1 and the processes in FIGS. 2-5 can be embodied as computer hardware circuitry or as a computer-readable program, or a combination of both. In another implementation, apparatus in FIG. 1 and the processes in FIGS. 2-5 can be implemented in an application service provider (ASP) system.

More specifically, in the computer-readable program implementation, the programs can be structured in an object-orientation using an object-oriented language such as Java, Smalltalk or C++, and the programs can be structured in a procedural-orientation using a procedural language such as COBOL or C. The software components communicate in any of a number of means that are well-known to those skilled in the art, such as application program interfaces (API) or inter-process communication techniques such as remote procedure call (RPC), common object request broker architecture (CORBA), Component Object Model (COM), Distributed Component Object Model (DCOM), Distributed System Object Model (DSOM) and Remote Method Invocation (RMI). The components execute on as few as one computer as in general computer environment 900 in FIG. 9, or on at least as many computers as there are components.

CONCLUSION

An annotator of an unambiguous boundary is described. A technical effect of the annotator is visually distinct graphical outlines of anatomical structure boundaries in healthcare images. The systems, method and apparatus described herein can be implemented in medical image viewing software. Although specific implementations have been illustrated and described herein, it will be appreciated by those of ordinary skill in the art that any arrangement which is calculated to achieve the same purpose may be substituted for the specific implementations shown. This application is intended to cover any adaptations or variations. For example, although described in procedural terms, one of ordinary skill in the art will appreciate that implementations can be made in an object-oriented design environment or any other design environment that provides the required relationships.

In particular, one of skill in the art will readily appreciate that the names of the methods and apparatus are not intended to limit implementations. Furthermore, additional methods and apparatus can be added to the components, functions can be rearranged among the components, and new components to correspond to future enhancements and physical devices used in implementations can be introduced without departing from the scope of implementations. One of skill in the art will readily recognize that implementations are applicable to future communication devices, different file systems, and new data types.

The terminology used in this application is meant to include all image processing and medical image acquisition environments and alternate technologies which provide the same functionality as described herein.

I claim:

1. A method to provide an unambiguous outline of a region of interest, the method comprising:
   identifying a mathematical boundary of a region of interest of an organ in a healthcare image in a memory; and
   generating a graphical object around the boundary in the image in the memory, the graphical object having varying degrees of opacity that are based on a distance of the graphical object from the boundary of the region of interest.

2. The method of claim 1, wherein the graphical object having varying degrees of opacity further comprises:
   a graphical object having varying degrees of uniformly tapering opacity.

3. The method of claim 1, wherein the graphical object having varying degrees of opacity further comprises:
   a graphical object having varying degrees of stepped tapering opacity.

4. The method of claim 1, wherein the varying degrees of opacity of the graphical object further comprises:
   having higher degree of opacity near the boundary and lesser degree of opacity further away from the boundary.

5. The method of claim 4, wherein the lesser degree of opacity further comprises: near complete transparency.

6. The method of claim 1, wherein generating the graphical object around the boundary in the image further comprises:
   creating in the memory a copy of the image; and
   generating the graphical object around the boundary in the copy of the image in the memory.

7. The method of claim 1, wherein generating the graphical object around the boundary in the image further comprises:
   selecting a color of the graphical object;
   selecting a maximum opacity of the graphical object;
   selecting a width of the graphical object;
   constructing the graphical object from the selected color, the selected maximum opacity and the selected width; and
   combine the constructed graphic object with the image.

8. The method of claim 1, wherein the graphical object has uniformly varying degrees of opacity between the mathematical boundary and an inner edge and an outer edge of the graphical object.

9. A non-transitory computer-accessible medium having executable instructions capable of directing a processor to perform:
   identifying a mathematical boundary of a region of interest of an organ in a healthcare image; and
   generating a graphical object around the boundary in the image, the graphical object having varying degrees of opacity that are based on a distance of the graphical object from the boundary of the region of interest.

10. The non-transitory computer-accessible medium of claim 9, wherein the graphical object having varying degrees of opacity further comprises:
    a graphical object having varying degrees of uniformly tapering opacity.

11. The non-transitory computer-accessible medium of claim 9, wherein the graphical object having varying degrees of opacity further comprises:
    a graphical object having varying degrees of stepped tapering opacity.

12. The non-transitory computer-accessible medium of claim 9, wherein the varying degrees of opacity of the graphical object further comprises:
    having higher degree of opacity near the boundary and lesser degree of opacity further away from the boundary.

13. The non-transitory computer-accessible medium of claim 12, wherein the lesser degree of opacity further comprises:
    near complete transparency.

14. The non-transitory computer-accessible medium of claim 12, wherein the higher degree of opacity further comprises:

near complete opacity.

15. The non-transitory computer-accessible medium of claim 9, wherein the executable instructions capable of directing the processor to generate the graphical object around the boundary in the image further comprise executable instructions capable of directing the processor to perform:

creating a copy of the image; and
generating the graphical object around the boundary in the copy of the image in the memory.

16. The non-transitory computer-accessible medium of claim 9, wherein the executable instructions capable of directing the processor to generate the graphical object around the boundary in the image further comprise executable instructions capable of directing the processor to perform:

selecting a color, maximum opacity and width of the graphical object; constructing the graphical object from the selected color, the selected maximum opacity and the selected width; and
combine the constructed graphic object with the image.

17. A system comprising:

a processor;
a storage device operable to store an image and the storage device being coupled to the processor; and
software apparatus operative on the processor to generate a graphical object around a boundary in the image, the graphical object having varying degrees of opacity that are based on a distance of the graphical object from the boundary of the region of interest.

18. The system of claim 17, wherein the graphical object having varying degrees of opacity further comprises:

a graphical object having varying degrees of uniformly tapering opacity.

19. The system of claim 17, wherein the graphical object having varying degrees of opacity further comprises:

a graphical object having varying degrees of stepped tapering opacity.

20. The system of claim 17, wherein the varying degrees of opacity of the graphical object further comprises:

having higher degree of opacity near the boundary and lesser degree of opacity further away from the boundary, and
wherein the lesser degree of opacity further comprises near complete transparency.

21. The system of claim 17, wherein the software apparatus operative on the processor to generate the graphical object around the boundary in the image further comprises software apparatus operative on the processor to:

create in the storage device a copy of the image; and
generate the graphical object around the boundary in the copy of the image in the storage device.

22. The system of claim 17, wherein the software apparatus operative on the processor to generate the graphical object around the boundary in the image further comprises software apparatus operative on the processor to:

construct the graphical object from a color, a maximum opacity and a width.

* * * * *